(12) United States Patent
Figueroa

(10) Patent No.: US 11,523,930 B2
(45) Date of Patent: Dec. 13, 2022

(54) SUPPORT STRAP SYSTEM AND METHOD OF USE

(71) Applicant: Alex Figueroa, Houston, TX (US)

(72) Inventor: Alex Figueroa, Houston, TX (US)

( * ) Notice: Subject to any disclaimer, the term of this patent is extended or adjusted under 35 U.S.C. 154(b) by 223 days.

(21) Appl. No.: 16/139,024

(22) Filed: Sep. 22, 2018

(65) Prior Publication Data
US 2019/0091058 A1 Mar. 28, 2019

Related U.S. Application Data

(60) Provisional application No. 62/562,254, filed on Sep. 22, 2017.

(51) Int. Cl.
*A61F 5/37* (2006.01)

(52) U.S. Cl.
CPC .................. *A61F 5/3723* (2013.01)

(58) Field of Classification Search
CPC ........ A61F 5/3723; A61F 5/028; A61F 5/026; A61F 5/37; A61F 5/01; A61F 5/0118; A61F 5/02; A61F 5/03; A61F 5/058; A61F 13/148; A61F 5/055; A61F 13/00038; A61F 13/145; A61F 2005/0183; A61F 2007/0024; A61F 2007/0228; A61F 2007/0231; A61F 2250/0004; A61F 5/3715; A47D 15/006; A47D 13/086; A41F 9/002; A41F 9/025; A41F 9/00; A41F 9/02; A41F 19/00; A41F 11/16; A41F 3/00; A41F 9/005; A41F 15/00; A41F 1/08; A41F 3/04; Y10S 128/19
See application file for complete search history.

(56) References Cited

U.S. PATENT DOCUMENTS

| | | | | |
|---|---|---|---|---|
| 1,755,641 | A | * | 4/1930 | Foulke ................ A61F 5/05808 602/19 |
| 5,259,833 | A | * | 11/1993 | Barnett ................... A61F 5/026 2/44 |
| 5,466,214 | A | * | 11/1995 | Calderon-Garciduenas ................ A61F 5/026 602/19 |
| 10,772,439 | B2 | * | 9/2020 | Law ..................... A47D 13/086 |

* cited by examiner

*Primary Examiner* — Ophelia A Hawthorne
(74) *Attorney, Agent, or Firm* — Leavitt Eldredge Law Firm

(57) ABSTRACT

A harness system includes a torso strap to fit around the torso of a wearer; one or more arm straps; a back strap extending between the torso strap and the one or more arm straps; two cuffs positioned opposite one another via the one or more arm straps; and a handle extending from the back strap; the two cuffs are to secure around the arms of the wearer; and the handle provides for a way to support the wearer.

2 Claims, 3 Drawing Sheets

SUPPORT STRAP SYSTEM AND METHOD OF USE

BACKGROUND

1. Field of the Invention

The present invention relates generally to harnesses and more specifically, to a harness utilized to retain an infant, child, disabled, and/or similar types of persons in a sitting position.

2. Description of Related Art

Harnesses are well known in the art and are commonly used to retain the infant at a specified walking distance from the parent. FIG. 1 depicts a simplified version of a harness system 101 having a harness portion 103 connected to a handle 105 via a lead 107. The harness can be secured to a child, while the user holds lead 105. Besides walking harnesses, there is no additional art that discloses harnesses utilized to retain infants, children, and/or other types of persons. There is a need for a harness to assist the parent, custodian, and other similar person to retain the infant in a stationary, sitting position. In addition, there is a need for a harness to retain children, elderly, disabled, or other persons in a stationary or sitting position.

Accordingly, although great strides have been made in the area of system and methods to retain infants, many shortcomings remain.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
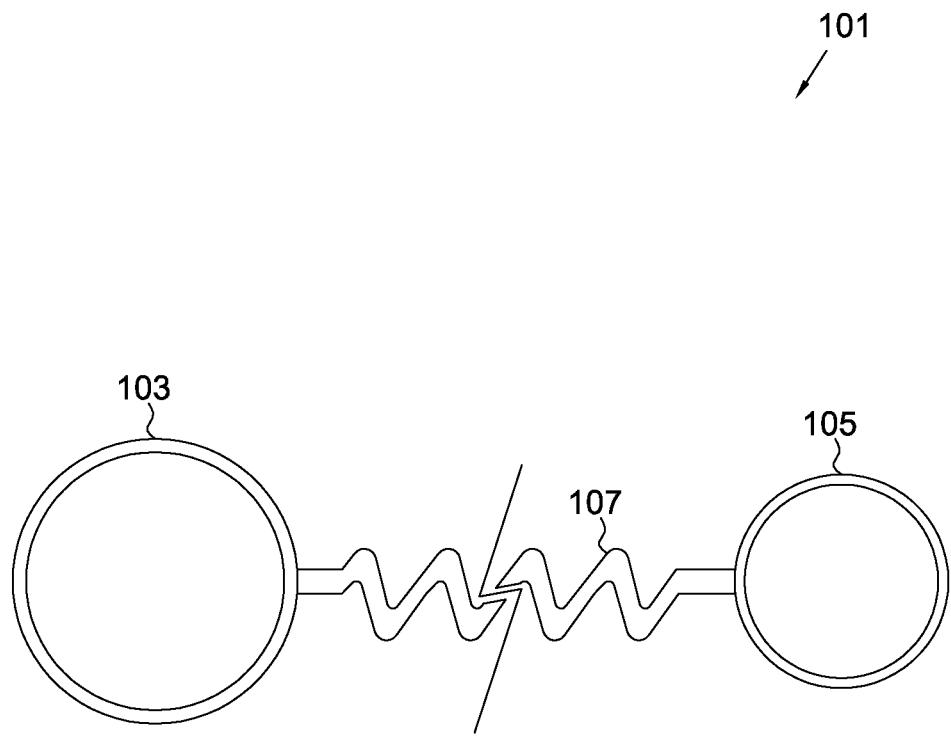
FIG. 1 is a simplified diagram of a common harness system.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional harness systems. Specifically, the present invention provides for a convenient harness to secure to a child or adult that aids in helping the wearer remain seated and/or upright. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Figure 2:
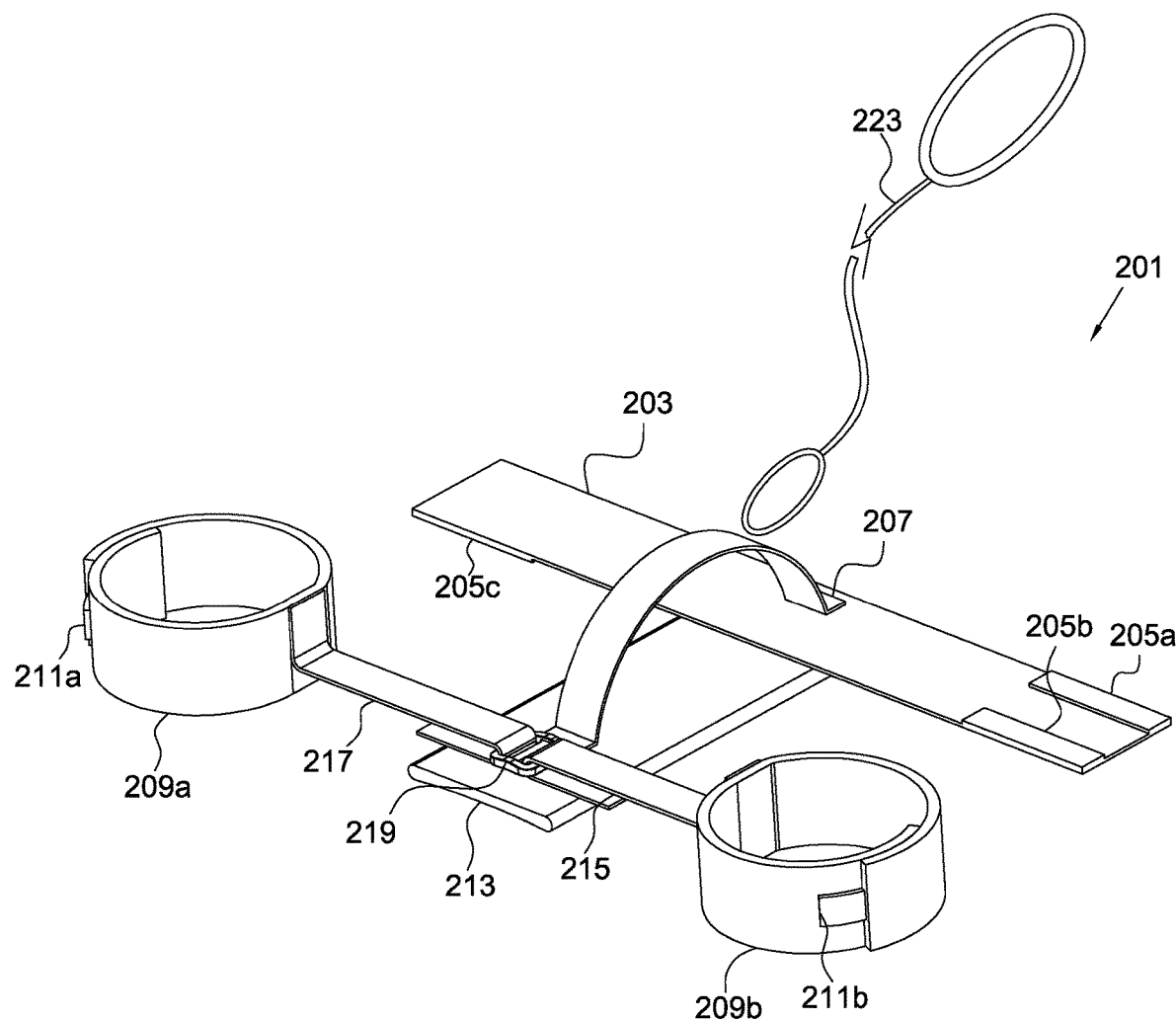
FIG. 2 is an oblique view of a harness system in accordance with a preferred embodiment of the present application.
Figure 3:
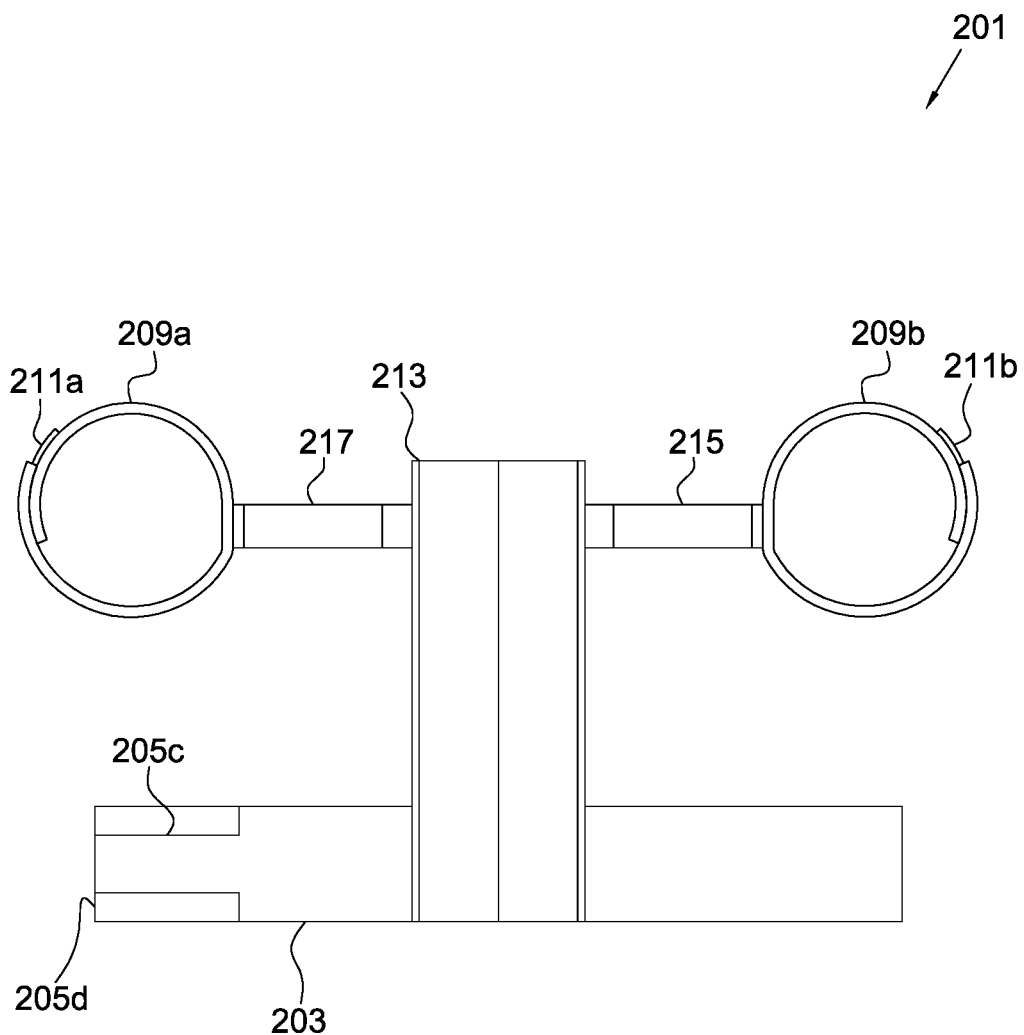
FIG. 3 is a front view of the harness system of FIG. 2.

Referring now to the drawings wherein like reference characters identify corresponding or similar elements throughout the several views, FIGS. 2 and 3 depict oblique and front views of a harness system 201 in accordance with a preferred embodiment of the present application. It will be appreciated that system 201 overcomes one or more of the above-listed problems commonly associated with conventional harness systems.

In the contemplated embodiment, system 201 includes a torso strap 203 configured to wrap around a torso of the wearer. A securement means 205a-c can be included thereon and configured to secure the strap in place around the torso. The securement means 205 is a hook and loop fastener in the preferred embodiment, but could alternatively be snaps, buttons, clasps, or the like.

System 201 further includes a handle 207 which is accessible by a parent, guardian, or other support person to help provide support to the wearer.

A back strap 213 extends from the torso strap to arm straps 215, 217 which has two cuffs 209a-b with closures 211a-b. In the preferred embodiment, the closures 211 are again hook and loop fasteners, but could be altered as desired.

In the preferred embodiment, the arm straps 215, 217 are adjustably secured to a buckle 219, which allows for adjustment to fit the wearer properly. It should be appreciated that the handle 207 can be secured above the buckle, or at various positions along the back strap 213.

System 201 further includes a leash 223 or other similar apparatus configured to secure to handle 207 and provide a means of control by the parent/guardian or the like.

It should be appreciated that the materials of the system can vary, and in addition, the cuffs 209 can include padding or the like for improved comfort.

It should be appreciated that one of the unique features believed characteristic of the present application, is the configuration of the back strap, torso strap, and arm cuffs, which provide for a harness system that can secure to an infant/child/disabled, and provide support in a sitting position.

In one embodiment, for example, the system is comprised of "1" shoulder adjustable cuffs which are padded and made with any material/fabric; "2" torso adjustable strap with 3 to 4 inches wide with fabric with VELCRO on one side; "3" fabric handle is used to hold on to and is secured above the top buckle and at the bottom of the padding at center of the torso strap; "4" padded fabric cover used to secure shoulder cuffs and strap and torso strap in position and to help pad against fingers holding fabric handle and to secure buckle for shoulder strap; "5" adjustable straps with one end VELCRO secured by plastic buckle that allows both shoulder straps to be adjusted for better fit; "6" buckle made of plastic with is secured at center top of padded fabric that is used to secure both shoulder cuffs and straps and allows adjustable means; "7" extra leash for walking.

During use, the cuffs are secured around the arms of the wearer and the arm straps can be adjusted via the buckle for the needed length. The handle is thereby positioned on the back of the wearer, and provides a convenient means for the parent/guardian, to use one hand to provided support, thereby keeping their other hand primarily free.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A harness system, comprising:
    a torso strap configured to fit around the torso of a wearer, the torso strap extending from a first end to a second end, the torso strap having a first fastener secured to the first end and configured to removably secure to a second fastener secured to the second end, the first fastener and the second fastener are configured to adjust the torso strap around a waist of a user;
    one or more arm straps;
    a back strap extending between the torso strap and the one or more arm straps;
    a buckle secured to the back strap and the one or more arm straps, the one or more arm straps are adjustable via the buckle;
    two cuffs positioned opposite one another via the one or more arm straps, the two cuffs are adjustably positioned at a distance relative to the back strap via the buckle;
    a handle extending from the back strap, the handle is secured to both the torso strap and the back strap; and
    a leash removably attached to the handle;
    wherein the two cuffs are configured to secure around the arms of the wearer; and wherein the handle provides for a means to support the wearer.

2. A method of supporting a person, the method comprising:
    providing the system of claim 1;
    securing the torso strap around the torso of the wearer;
    securing the two cuffs around the arms of the wearer; and
    using the handle to support the wearer.

* * * * *